United States Patent [19]
Barot

[11] Patent Number: 5,807,244
[45] Date of Patent: Sep. 15, 1998

[54] SINGLE USE DISPOSABLE IRIS RETRACTOR

[76] Inventor: Jagdish Shantilal Barot, 1708 Pineda St., Cocoa, Fla. 32922

[21] Appl. No.: 749,536

[22] Filed: Nov. 15, 1996

[51] Int. Cl.$^6$ .................................................... A61B 11/02
[52] U.S. Cl. ........................................... 600/236; 606/107
[58] Field of Search ................................ 600/201, 203, 600/209, 210, 217, 227, 235, 236; 606/107, 151, 166, 191, 198, 201

[56] References Cited

U.S. PATENT DOCUMENTS

| 3,857,386 | 12/1974 | Ashbell | 600/236 X |
| 4,579,116 | 4/1986 | Catalano | 600/236 X |
| 4,991,567 | 2/1991 | McCuen, II et al. | 600/236 X |
| 5,514,076 | 5/1996 | Ley | 600/236 X |

*Primary Examiner*—Beverly M. Flanagan
*Attorney, Agent, or Firm*—Law Offices of Brian S. Steinberger; Brian S. Steinberger

[57] ABSTRACT

A single use disposable iris retractor tool. The device is flexible at the hook portion end with a sufficient stiffness added to a long leg of the hook for ease of holding during insertion in an eye. A smooth exterior sleeve can be used for adding the stiffness. Alternatively, grooves can be formed on the sleeve. The sleeve can be adhered to the long leg. Alternatively, an angled or looped end on the long leg can hold the sleeve in place. An another alternative does not use a sleeve but instead has an enlarged diameter on the long leg with a grooved exterior. A transparent storage tube can be used that allows the surgeon to view the orientation and location of the hook. The tool helps surgeons control anterior vaulting of retracted iris thus eliminating the obstruction ton the surgical incision. The device also has more clamping power to secure it in position than the other comparative devices currently in use.

19 Claims, 9 Drawing Sheets

SINGLE USE DISPOSABLE IRIS RETRACTOR

This invention relates to surgical devices, and in particular to a safe and effective surgical device that is used for temporary mechanical retraction of an iris to dilate a small pupil in ocular surgical procedures when the pupil dilation is not achieved by pharmacological methods.

BACKGROUND AND PRIOR ART

Surgical eye operation procedures have generally used flexible hook ended iris retractors made from very flexible rod like polymer monofilaments having clamping devices on opposite ends. These retractors are cumbersome to insert into small incisions since the retractors lack sufficient stiffness. Upon retraction of an iris, the lack of stiffness in the long leg of a retractor can result in the anterior vaulting of a retracted iris because of a push from the retracted iris towards the vertical direction. This anterior vaulting tends to block the surgical incision which is in the same limbal plane as are the stab incisions through which iris retractors are inserted into an eye. Generally, the surgeons must improvise on the spot to repress the vaulting, which results in the retracted iris sliding out of the hook vaulted towards the vertical direction. This problem generally requires a surgeon to interrupt the surgery to re-grasp and retract the iris.

In many cases of surgical eye operation procedures, the iris retractors slide inwards through the clamping device because of the opposing force exerted by the retracted iris. This is due to an insufficient clamping force exerted by the clamping devices on the monofilament because of it's smooth and slippery surface. Upon completion of the surgical procedure, it is cumbersome for surgeons to release the retracted iris from the hook and remove the iris. Because the iris retractor is flexible, a surgeon cannot simply hold (with forceps) the device from the long leg or stem (external to the eye) and push it inwards towards the center of the pupil. Surgeons must first push the clamping device towards the tail end to create enough stem-length between the corneal incision and the clamping device, then hold the retractor from the stem-length, and then push it in, and possibly repeat the process until the retracted iris is released. Alternatively, to save time, surgeons must simply pull the iris retractor out to take advantage of the flexibility of the hook that will straighten and release the iris. This latter method can be dangerous because of possible lacerations to the delicate iris.

Known prior retractors used in the eye surgery procedures include U.S. Pat. No. 5,174,279 to Cobo et al. and the American Journal of Ophthalmology, vol. 110, p. 577 of Nov. 15, 1990.

Thus, the need exists to overcome these shortcomings in the prior art.

SUMMARY OF THE INVENTION

The first objective of the present invention is to provide an ocular surgical tool for the mechanical retraction of an iris having a grippable exterior surface for clamping the iris.

The second object of this invention is to provide a provide an ocular surgical tool for the mechanical retraction of an iris having a stiffening sleeve around the device.

A preferred embodiment of the surgical tool is made of a flexible rod like monofilament with a sleeve on the long leg that provides it with added stiffness on the stem. The sleeve further adds thickness to the stem for increasing the traction of the elastic clamping lug on the stem. The device includes a monofilament with a hook formed at one end, a sleeve about the long end of the monofilament, and a clamping lug.

Further objects and advantages of this invention will be apparent from the following detailed description of a presently preferred embodiment which is illustrated schematically in the accompanying drawings.

BRIEF DESCRIPTION OF THE FIGURES

FIG. 6b shows the iris retractor made from the monofilament shown in the FIG. 6a.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

Figure 1:
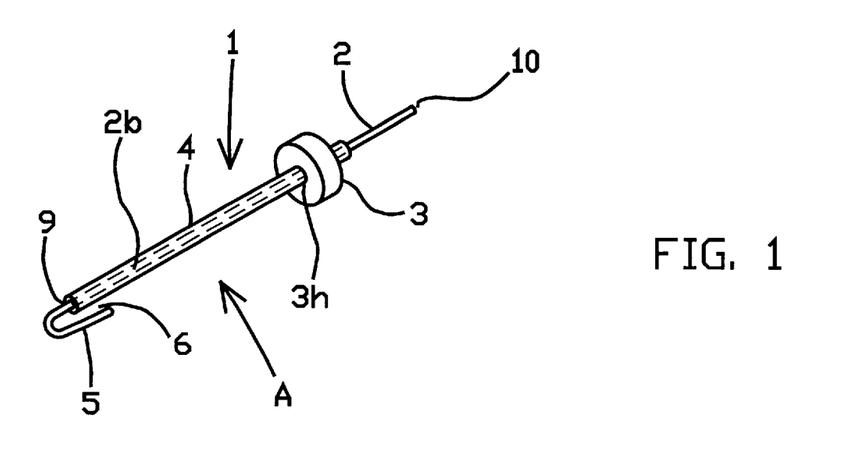
FIG. 1 is a perspective view of the iris retractor invention.
Figure 2:
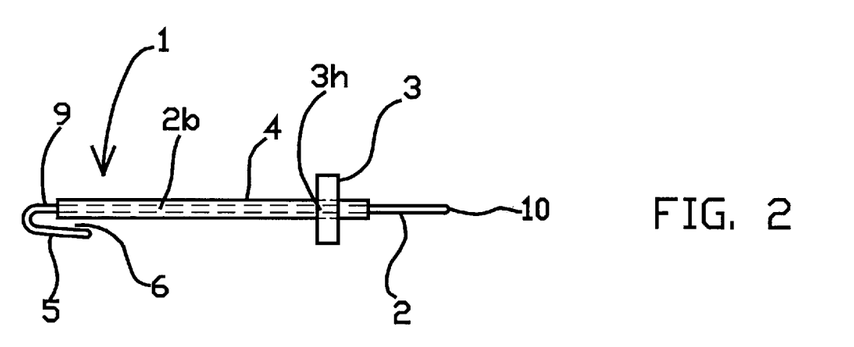
FIG. 2 is the side view of the iris retractor invention of FIG. 1 along arrow A.
Figure 3:
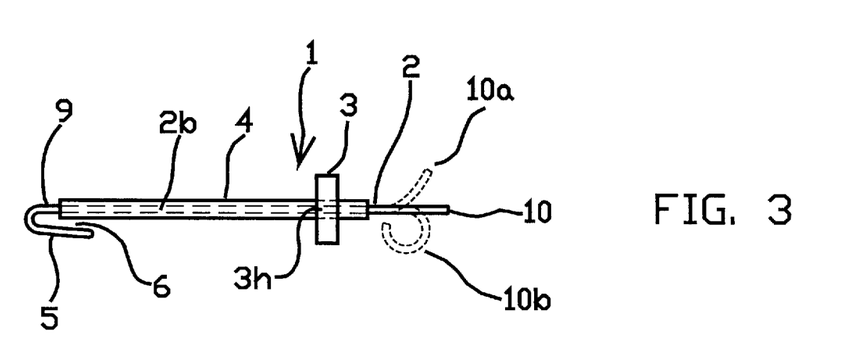
FIG. 3 is the side view of the iris retractor invention of FIG. 2 along arrow A with an alternative tail-end configuration of the monofilament shaft.

Referring to FIGS. 1–3, a fully assembled iris retractor 1 can include a round monofilament 2 made of bio-compatible plastic or polymer that is bent in approximately a U-shape or V-shape 6 at one end and the other end of the monofilament is either straight 10, looped 10b or angled 10a. (The loop 10b or angled end 10a will lock the sleeve in place on the long leg 2b of the device thus prevent it from falling off.) The monofilament 2 is shown separately in FIGS. 7a–7b. The monofilament 2 can be made from a polymer that is relatively flexible and can bend easily with slight exertion of force. Bio-compatible materials are inert to bio-chemistry, will not cause detrimental side effects and through tests are approved by the Food & Drug Administration of the United States of America for invasive surgical procedures or for devices for implant in the human body.

A second component of the iris retractor 1 is a sleeve 4, of a tubular cylindrical shape made from bio-compatible polymer plastic or metal with sufficient wall thickness (described later) making it stiffer than monofilament 2, and has a hole 4a through it (as shown separately in FIG. 8).

Figure 10:
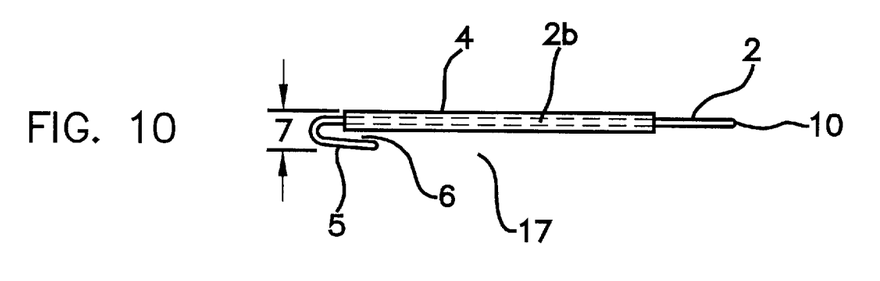
FIG. 10 illustrates a the partially assembled iris retractor of FIG. 2 with the monofilament inserted through the hole in the cylinder sleeve.

A third component of the iris retractor 1 is a clamping lug 3 that is flexible, soft and elastic, and is cut into tiny round or rectangular pallet like tablets. Different configurations of the clamping lug 3 are shown FIGS. 9a through 9d. The clamping lug 3 is wider around the axis of the long leg 2b of the hook assembly 17, as shown in FIG. 10. The thickness of the clamping lugs 9a–9d can be between approximately 0.75 mm to approximately 1.5 mm with maximum width/diameter of approximately 2 mm made from synthetic rubber, latex or silicone.

The monofilament 2 is inserted through the hole 4a of the sleeve 4 so that the hook 6 is at one end of the sleeve 4 and the straight end 10 (or tail end) of the monofilament 2 is visibly out of the other end of the sleeve 4. The outer diameter of the monofilament 2a is only slightly smaller than the inner diameter of the sleeve 4 for a snug fit.

Figure 4:
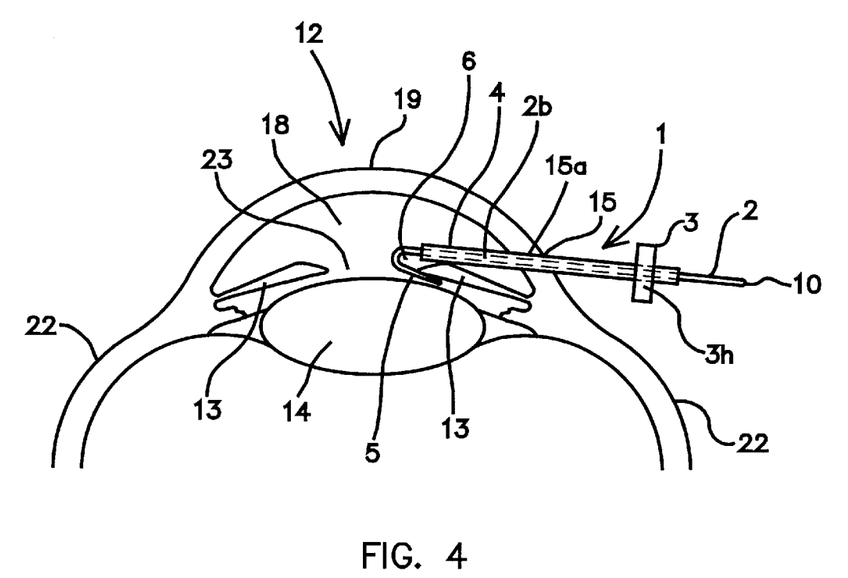
FIG. 4 is a cross-sectional side view of an eyeball with the iris retractor invention inserted inside the eye through an incision in limbus with the hook grasping the rim of the iris.
Figure 5:
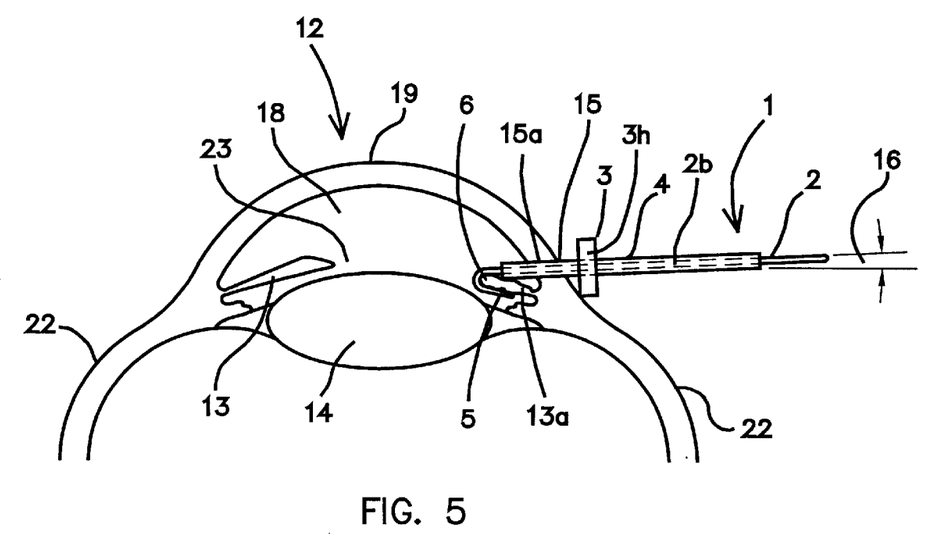
FIG. 5 is a cross-sectional view of the eyeball with iris in the retracted position with the clamping lug acting as a stopper.

FIG. 10 illustrates the assembly 17 of the monofilament 2 and the sleeve 4. The sleeve 4 provides strength to the long leg 2b of the monofilament 2 thus making it relatively stiffer and more resistant to bending when subjected to the same amount of force under which the monofilament 2 alone can easily bend. The assembly 17 with the sleeve 4 can be made from plastic or polymer, and can be handled in the serrated jaws of any forceps used in ocular surgery. Because the polymer is more elastic than metal, it temporarily reforms to adapt to the forces of the jaws of the forceps when they close in on it, and adhere to the grooves of the serrated jaws of the forceps, thus virtually eliminating any chances of slippage during insertion into an eye 12 and during surgical maneuvering. The added stiffness also makes the device easier for insertion in anterior chamber 18 of an eye 12 through a small incision 15a of approximately 0.50 mm in the limbus 15 because it will not bend as easily as does using a single diameter rod of the monofilament 2, as shown in FIGS. 4–5.

Referring to FIG. 3, forming the tail end 10 into a loop 10b or angled end 10a will lock the sleeve in place on the long 2b of the device that will prevent it from sliding out and falling off. It is secured from the other end with the hook 6.

Referring to FIGS. 1–10, the assembly 17 is inserted through the stab hole 3h approximately in the center of the clamping lug 3. The clamping lug 3 can slide along the sleeve 4. The clamping lug 3, being elastic, provides better traction and more friction on the sleeved portion of the long leg 2b because of the added thickness of the long leg 2b due to sleeve 4 than when the said clamping lug 3 is used on a single diameter monofilament 2a without sleeve 4. As a result, the retractor 1 will better hold the retracted iris 13a in a retracted position due to more clamping power from the lug 3, and will not slide inwards during surgery. Thus, the invention will essentially eliminate a reason to interrupt surgery to re-adjust the retraction of iris 13 during surgery.

Figure 7A:
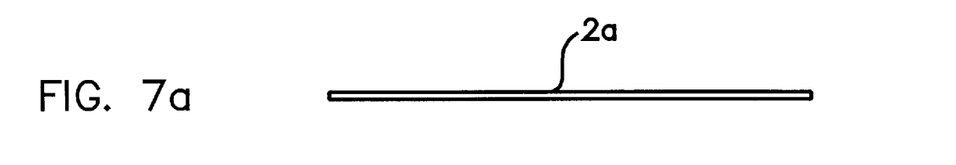
FIG. 7a illustrates a rod like monofilament.
Figure 7B:
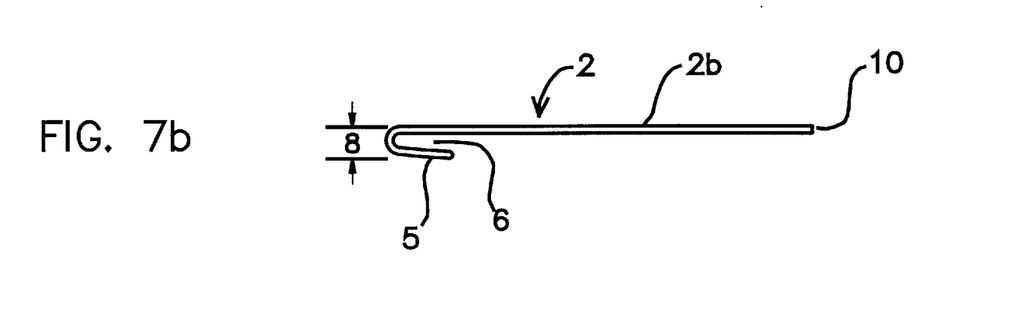
FIG. 7b shows the monofilament of FIG. 7a with a short leg shaped as a hook and a long leg.
Figure 8:
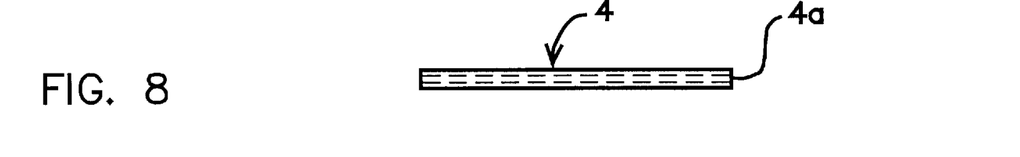
FIG. 8 is a side view of the cylinder like sleeve for the iris retractor invention.
Figure 9A:
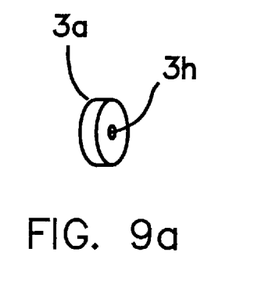
FIGS. 9a–9d illustrate different configurations of the clamping lug used with the iris retractor invention.
Figure 9B:
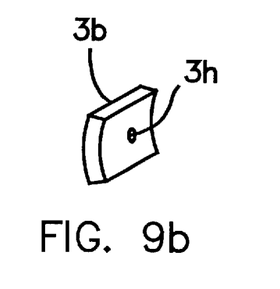
Figure 9C:
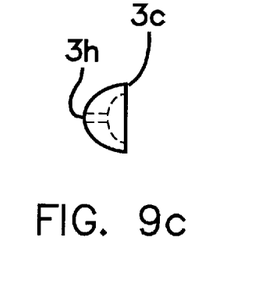
Figure 9D:
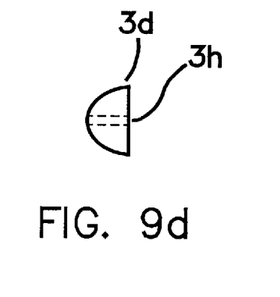

Referring to FIGS. 7a and 8, the monofilament 2a can have the diameter of approximately 0.10 mm to approximately 0.14 mm (same as 5-0 Nylon suture material). The sleeve 4 can be made from tubes of plastic (such as polycarbonate, PEEK or polyamide), which are approved by the Food and Drug Administration for invasive surgical uses in humans because they are bio-chemically inert materials. Other metal materials can be used such as ferrous alloys of stainless steel, or non-ferrous metal alloys such as titanium, molybdenum, and the like. The wall thickness of the plastic sleeve 4 can range from approximately 0.030 mm to approximately 0.060 mm and the outer diameter of the sleeve 4 can be less than approximately 0.30 mm. Thus, the larger the wall thickness of the sleeve 4, the stiffer it is.

Referring to FIGS. 1–10, the relative stiffness of iris retractor 1 with added stiffness of the long leg 2b due to sleeve 4 has a major advantage over the iris retractors made from a single diameter rod of monofilament 2a alone. Because it is sufficiently stiff to resist bending when it is subjected to normal forces encountered during ocular surgical procedure, the hook 5 can be vaulted towards posterior by moving clamping lug 3 closer to limbus 15, whereupon the lug 3 will rest on sclera 22 external to the eye 12 thus uplifting it external to the limbus 15 where a transition in curvature of eyeball 12 occurs. This is possible because the clamping lug 3 is made wider and its periphery is sufficiently far around the axis of the assembly 17 of the sleeve 4 and monofilament 2. Because of the sufficient stiffness provided by the sleeve 4, the iris retractor 1 will not bend at the limbus incision 15a when subjected to normal forces during surgical procedures. The posterior vaulting of retracted iris 13a is depicted in FIG. 5 by angle 16. The ability to adjust vaulting of retracted iris 13a is very important during surgery to control excessive anterior vaulting (which is very common with the flexible iris retractors made from monofilament alone) that tends to block surgical access, which requires extra surgical maneuvers to clear the blockage thus consuming more time. Anterior vaulting occurs when the stem or the long leg 2b of the device 1 is too flexible to resist a push from the retracted iris 13a towards vertical. Because of the stiffness in the stem or long leg 2b of the invention 1, a push from retracted iris 13a will be insufficient to vault the hook 6 towards anterior. This will save precious surgical time and frustrations on the part of surgeons. When anterior vaulting of the retracted iris 13a occurs, the said retracted iris 13a slips out of the hook 6 requiring the surgeon to interrupt the surgery to re-grasp the iris 13 into the hook and repeat retraction. This consumes even more time adding to the surgeons' frustrations. Ideally the surgical time must be at the most minimum time possible.

Referring to FIGS. 1–10, the sleeve 4 can be placed properly along the stem of the monofilament 2 to adjust length 9 (outside the sleeve 4) of the monofilament 2 at the hook end as desired. The shorter the length 9, the stiffer it tends to be without affecting the flexibility of the short leg 5 of the hook 6.

Referring to FIGS. 1–10, the sleeve 4 can be thermally fused or chemically bonded with solvent or glue to the monofilament 2 to secure it in position over the monofilament 2. If not bonded, the sleeve 4 can be secured in the position along the long leg 2b by providing a bend 10a or loop 10b at the tail end 10 of the hook monofilament 2. This, combined with the formation of the hook 6 at the other end, will secure the sleeve 4 in the long leg 2b of the hook 2 and prevent it from sliding and slipping out from the monofilament 2 during normal use.

Figure 11A:
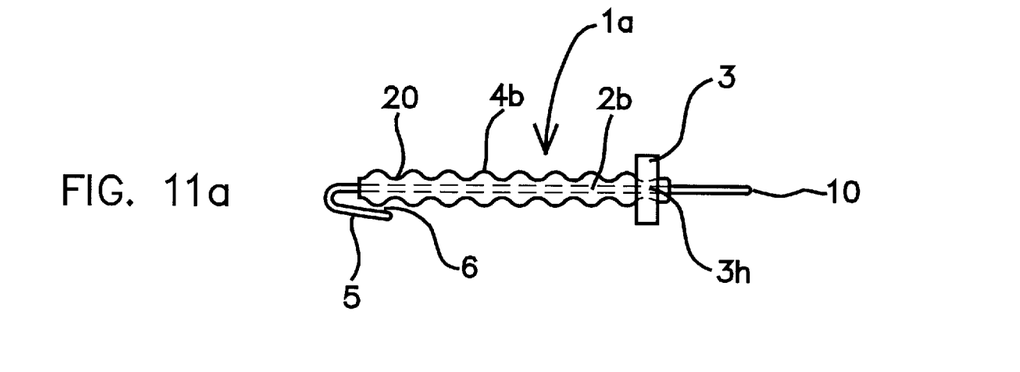
FIG. 11a illustrates the iris retractor invention of FIG. 2 with alternative sleeve with grooves around the sleeve.
Figure 11B:
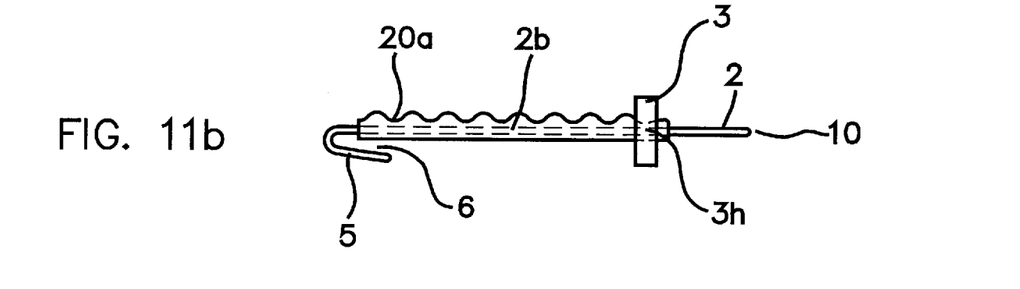
FIG. 11b illustrates the iris retractor invention of FIG. 11a with grooves on one side of the sleeve.
Figure 12:
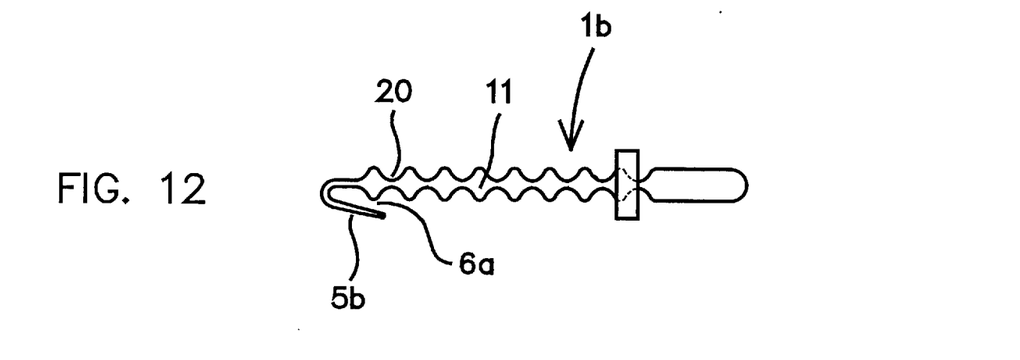
FIG. 12 illustrates an iris retractor without a sleeve, wherein grooves are formed on the long leg of the hook forming a thicker stem for added stiffness.
Figure 13:
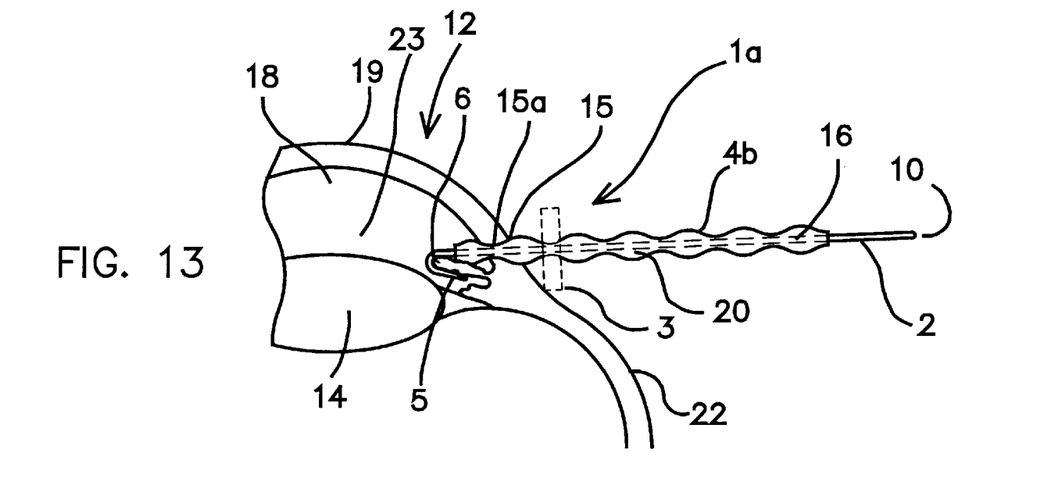
FIG. 13 shows the iris retractor held in position by the periphery of the limbal incision in the limbus region of an eye closing in on a groove of the long leg of the iris retractor of the preceding figures.
Figure 14:
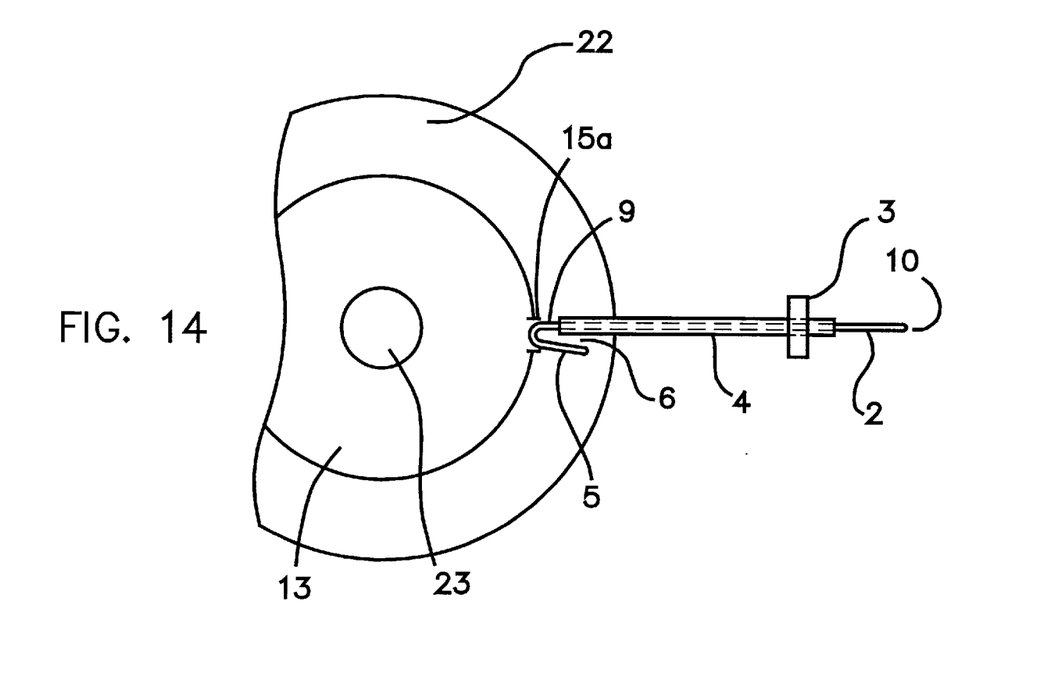
FIG. 14 shows a top view of the eyeball with the iris retractor at the incision in limbus.
Figure 15:
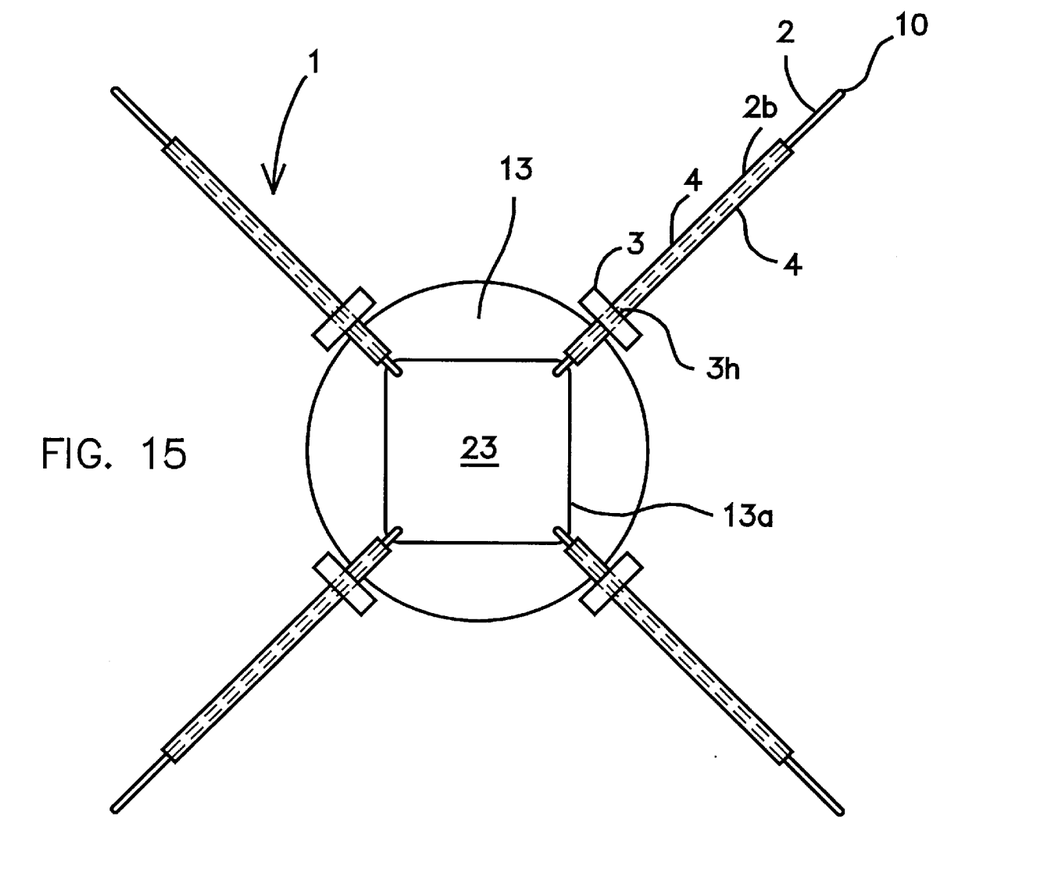
FIG. 15 shows the top view of the eye with iris retracted in four quadrants thus mechanically dilating the pupil in four quadrants of an eye.
Figure 18:
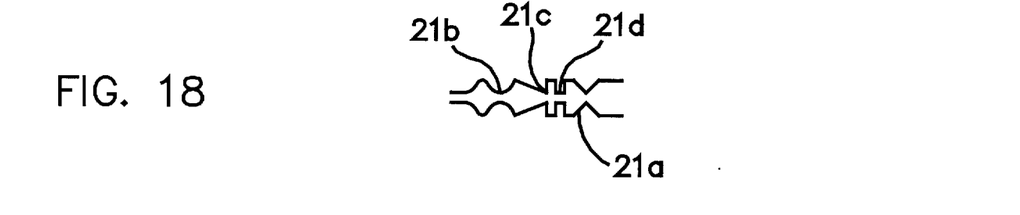
FIG. 18 illustrates another exterior view of the groove shapes on the sleeve and on the long leg of the hook that can be symmetric or asymmetric on the sleeve for control of vaulting.

Referring to FIGS. 11a, 11b and 12, the sleeve 4 can also be fabricated to have one or more grooves 20–21. These grooves 20, 20a and 21a–21d can be utilized to have the iris retractor 1 snugly fit in the incision 15a in limbus with the periphery of incision 15a closing in on the grooves, thus holding it in the position as shown in FIG. 13. In this instance the clamping lug 3 can be utilized only to adjust the vaulting of the retracted iris 13a as described above causing the grooves 20, 20a, 21a–21d to prevent the device 1 from sliding in by acting as a stopper. By making the grooves 20, 21 and 21a–21d in appropriate shape as shown in FIG. 18, the grooves themselves can be used to control vaulting of iris 13 thus eliminating the need for clamping lug 3 altogether.

Figure 6A:
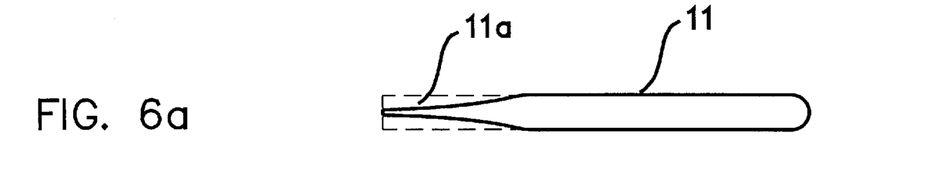
FIG. 6a shows a monofilament with thicker portion of the long leg for greater stiffness, with the end reduced down to the diameter of monofilament of FIG. 7a for flexibility.
Figure 6B:
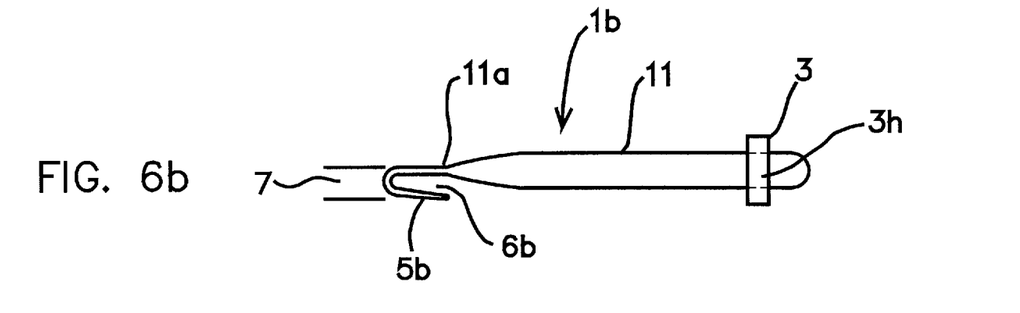

Referring to FIGS. 6a–6b, thicker and less flexible monofilament 15 can also be utilized for added stiffness of the stem or long leg 11. The end 11a of the thicker monofilament 11 can be mechanically (by process of sanding, grinding, or stretching it beyond elastic limit) or chemically (by using solvents) tapered or thinned to reduce the stiffness which then can be bent into a flexible hook 6a having stiffer long leg or stem 11. This essentially eliminates the need for the sleeve 4 as for the iris retractor 1b. Alternatively, the long leg and the hook of iris retractor 1b can be plastic formed from injection molding and the like.

A portion of monofilament 2a that will make up the long leg or stem 2b can be made stiffer by an externally applied coating adhesive spray or by dipping it into thermally melted plastic that will adhere to and set on its surface.

Referring to FIGS. 11a–11b, the sleeve 2 can also be fabricated to have one or more grooves 20 on either only one side 20a or two sides or all around the diameter of the sleeve 4. Upon insertion into an eye 12, the periphery of incision 15a closes in on the grooves 20 or 20a. The grooves 20 and 20a acting as a stopper at limbal incision 15a stops iris retractor 1 from sliding in and keeps retracted iris 13a in retracted position without clamping lug 3. In this instance, the provision and use of clamping lug 3 is optional for clamping use. However, it may still be utilized to control anterior vaulting of retracted iris 13a.

Referring to FIG. 18, by making the grooves 20, 20a and 21a–d in selected shapes, the grooves themselves can be used to control angle of vaulting 16 of device 1 and retracted iris 13a thus eliminating the need for clamping lug 3 altogether. The appropriate shape of the grooves can be "V" 21a, buttress groove 21b, "U" 21c, "square/rectangular" 21d, and by varying the opening angle of the said grooves, the angular contact between the periphery of incision 15a. The grooves can be varied to give various angles of vaulting. The width of the grooves can be made slightly larger than the thickness of cornea 19 at limbus 15. The total outer diameter of the stem 2b can still be maintained within 0.30 mm.

Figure 19:
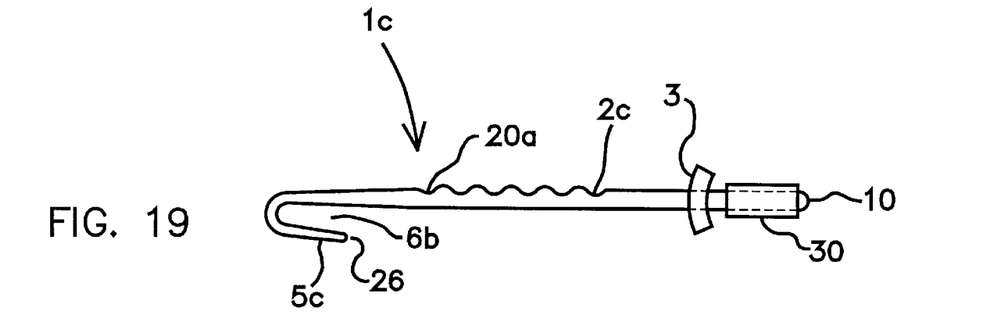
FIG. 19 shows hook made from a metal wire with grooves only on one side of the long leg, and a nonslip tube at the tail end.
Figure 20:
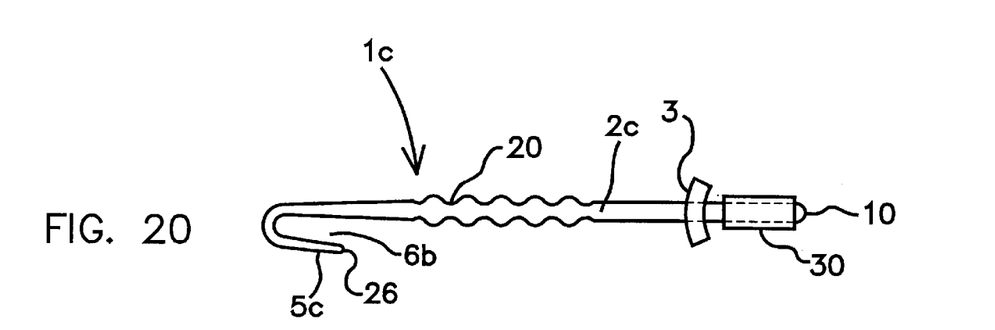
FIG. 20 shows a hook made of metal wire with grooves around the long leg and a nonslip tube surface at the tail end.
Figure 21:
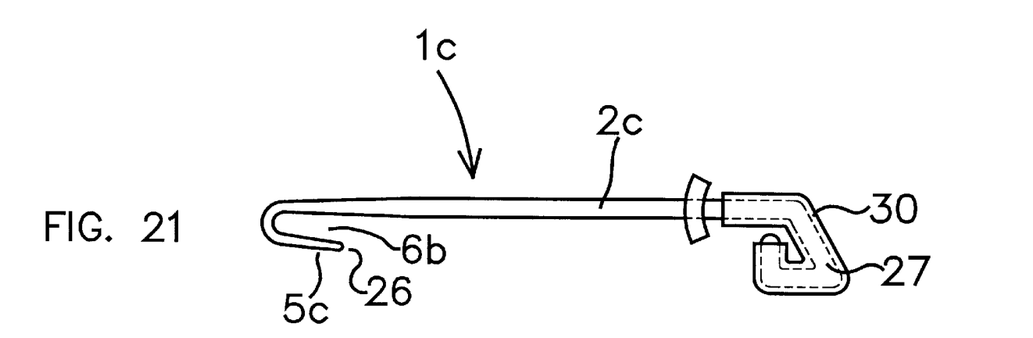
FIG. 21 shows the iris retractor made from a metal wire with the hook end tapered to a "U" shape interior with a "V" shape mouth opening, and a loop at the tail end of the long leg for the convenience of holding the retractor where the loop is covered with heat shrink tubing.

Referring to FIGS. 19–21, the device 1 can be made from metal rod-like wire from bio-compatible metal alloys such as titanium, molybdenum, stainless steel, and the like, that is sufficiently stiff to prevent any permanent damage to the form of the device when it encounters normal forces during ocular surgery. The wire of approximately 0.30 mm can be tapered down to approximately 0.12 mm near to one end, and all the way down to approximately 0.05 mm closer to the tip 26 at the same end. The dual tapered end makes it possible to form a "U" shaped hook 6b with "V" shaped opening. The tip 26 is free of any sharp edges. The tip 26 being very thin enables a surgeon to insert the tip 26 between iris and lens to scoop up and grasp the rim of the iris 13 into the hook 6b. The tail end 27 of the iris retractor 1c can be formed into a triangular 27 or rectangular (not shown) or any other geometrical shape with at least two non adjacent sides slightly apart to conveniently hold the device 1c firmly and securely in the crisscross serrated jaws of forceps to prevent any slippage or swiveling during insertion into an eye 12 and subsequent maneuvering of the device 1c. This holding loops 27 can be oriented at any convenient angle with the axis of the stem or long leg 2c and can be in any plane. The tail end 10b of the metal device 1c can be equipped with soft heat shrink tubing sleeve 30 that will shrink and adhere to the surface of the tail end 10. When held in forceps, it will temporarily reform to adhere to the shape of serration of forceps' jaws for added traction. The tapered hook 6b can be made into approximately "U" shaped hook 6b approximately 0.30 mm deep, with "V" shaped opening for ease of grasping the rim of iris 13 into the hook for retraction. For ease of insertion through a small incision of approximately 0.50 mm, the width of the hook can be confined to less than approximately 0.50 mm. Again, the use of clamping device 3 is rendered optional as discussed above. Because short leg 5c of the metal hook 6b is not flexible, the metal iris retractors 1c can be utilized to achieve maximum iris retraction. This is possible because the depth of the hook 6b is only approximately 0.30 mm, which is very short as compared to approximately 0.60 mm to approximately 0.80 mm for the flexible hooks 6.

Another major advantage of the stiffer stems or long legs of iris retractors 1, 1a, 1b, 1c is that upon completion of surgery, the surgeons can very conveniently hold the device from the stem external to an eye 12, and simply push the iris retractors inwards towards the center of the pupil 23 to release retracted iris 13a from the hooks. Because of the stiff stems, the devices 1, 1a, 1b and 1c will not bend when pushed through the clamping lug 3 and corneal incision 15a.

Referring to FIGS. 1–10, the sleeve 4 can be thermally or chemically bonded to the monofilament 2 to secure it in position over the monofilament 2. If not bonded, the sleeve can be secured in the position by providing a bend 10a or loop 10b at the tail end 10 of the monofilament 2. This combined with the formation of the hook 6 at the other end will secure the sleeve 4 on the long leg 17 of the hook 2 and prevent it from sliding out and separating from the monofilament 2 during normal use.

Referring to FIGS. 6a–6c, the monofilament 2 can be made stiffer by an externally applied coating on the monofilament 2. Thicker and less flexible monofilament 11a can also be utilized for added stiffness. The ends 11b and 11c of the thicker monofilament 11a can be mechanically or chemically tapered or thinned to reduce stiffness which can be bent into a hook 11c. This would give a device with flexible hook 11c and stiffer stem 11.

Figure 16:
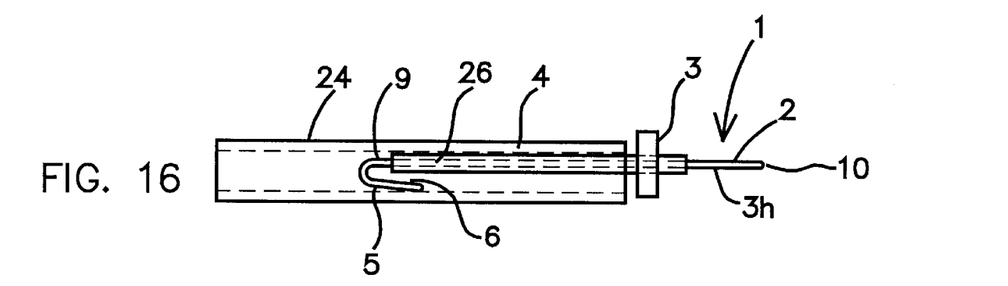
FIG. 16 illustrates the iris retractor stored in the transparent tube with the hook and the stem inside the tube clearly visible through the wall of the storage tube.
Figure 17:
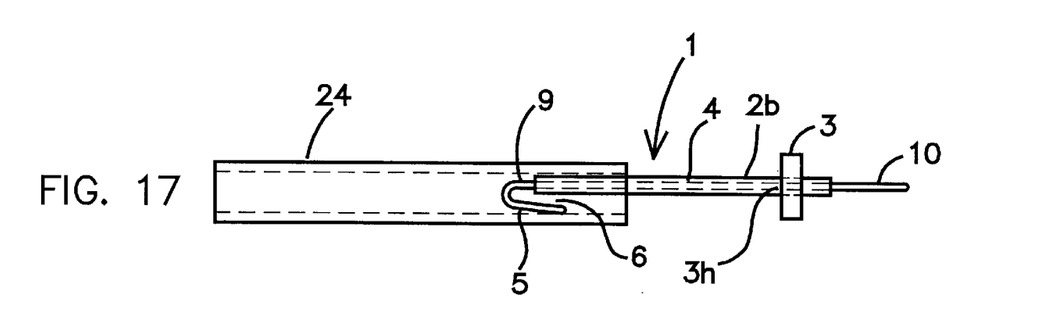
FIG. 17 shows an iris retractor partially pulled out of the storage tube for holding by forceps prior to surgical insertion into an eye.

Referring to FIG. 16, the iris retractors 1 can be stored in the transparent cylindrical storage tube 24 with the hook 6 inside the storage tube 24 with the substantial portion of the stem or the long leg 2b of the said iris retractor 1 also inside the said storage tube 24 clearly visible through the transparent walls of the said storage tube 24. Surgeons can view through the transparent walls to verify the orientation of the hook 6. The whole storage tube 24 can be oriented to orient the hook 6 for as deemed convenient, the device 1 can be partially pulled out as shown in FIG. 17, and it can be conveniently held from the stem or long leg 2b for insertion into anterior chamber 18 of an eye 12. The storage tube 24 being open at both the ends allows the transfer and even distribution of heat for autoclaving, or diffusion of ethylene oxide or peroxide gas for chemical sterilization. The inner diameter of the storage tube 24 can be equal to or less than the outer width 7 of the device 1 at the hook end 6 and substantially less than the width of the clamping lug 3. The sleeves and the thick version of the long leg embodiment using plastic materials can be formed from molds.

FIGS. 19–21 illustrate a retractor embodiment 1c with a all metal long shaft 2c.

Referring to FIG. 19, grooves 20a are on one side of thickened metal shaft 2c. Hook 6b tapers off shaft 2c at both 5c to rounded tip 26. Hook 6b has a U-shaped interior surface and a V-shaped mouth opening. Non slidable surface 30 on protruding end 10 can be heat shrunk plastic or elastomer such as rubber and the like, for aiding being held by a surgeon's forceps.

Referring to FIG. 20, this version is similar to that of FIG. 19, with the addition of having grooves on both the top and bottom of the long metal shaft 2c, or alternatively grooves are all the way around the shaft.

Referring to FIG. 21, this version corresponds to FIGS. 19–20, but metal shaft 2c does not have grooves, and shaft 2c has a downward facing loop end 27, with non slidable surface 30.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A single use ocular surgical tool for the mechanical retraction of an iris by an incision in the iris, comprising:
    a longitudinal flexible shaft having a first end and a second end;
    a hook formed at the first end of the shaft;
    a flexible plastic stiffening sleeve about the longitudinal shaft substantially between the hook and the second end of the shaft, the sleeve having an outer diameter of less than approximately 0.5 mm and being forcep held; and
    a clamp lug for gripping about the exterior of the stiffening sleeve adjacent to the second end of the shaft, wherein the hook and the clamp lug mechanically retract the iris without causing anterior vaulting of the retracted iris.

2. The single use ocular surgical tool of claim 1, wherein the longitudinal flexible shaft with the hook includes:
    a metal body.

3. The single use ocular surgical tool of claim 1, wherein the longitudinal flexible shaft with the hook includes:
    a plastic monofilament.

4. The single use ocular surgical tool of claim 1, wherein the hook is chosen from:
    a U-shape and a V-shape.

5. The single use ocular surgical tool of claim 1, wherein the second end of the shaft includes:
    a straight end and the sleeve is adhered to the longitudinal shaft.

6. The single use ocular surgical tool of claim 1, wherein the second end of the shaft includes:
    an angled end for locking the sleeve onto the longitudinal shaft.

7. The single use ocular surgical tool of claim 1, wherein the second end of the shaft includes:
    a looped end for locking the sleeve onto the longitudinal shaft.

8. The single use ocular surgical tool of claim 1, wherein the stiffening sleeve includes:
    a cylinder, wherein the second of the longitudinal shaft protrudes from the cylinder.

9. The single use ocular surgical tool of claim 1, further comprising:
    a non sliding surface about the second end of the shaft.

10. The single use ocular surgical tool of claim 9, wherein the non sliding surface is chosen from at least one of:
    plastic and rubber.

11. The single use ocular surgical tool of claim 1, wherein the stiffening sleeve includes:
    grooves in the exterior of the sleeve.

12. The single use occular surgical tool of claim 1, wherein the sleeve includes:
    a wall thickness of approximately 0.030 mm to approximately 0.060 mm; and
    an outer diameter of less than approximately 0.30 mm.

13. A single use ocular surgical tool for the mechanical retraction of an iris comprising:
    a longitudinal shaft having a flexible short first end portion and a thicker stiffer longer second end portion, the thicker second end portion having grooves on an exterior surface;
    a hook formed at the first end portion of the shaft; and
    a clamp lug for gripping about the exterior of the thicker second end of the shaft, wherein the hook and the clamp lug mechanically retract the iris without causing anterior vaulting of the retracted iris.

14. The single use ocular surgical tool of claim 13, wherein the thicker second end portion includes: an exterior coating over a filament.

15. The single use ocular surgical tool of claim 13, wherein the hook includes:
    tapered sections that yields a U-shaped hook interior and V-shaped mouth opening.

16. The single use ocular surgical tool of claim 13, wherein the shaft is: plastic.

17. The single use ocular surgical tool of claim 13, wherein the shaft is: metal.

18. The single use ocular surgical tool of claim 13, wherein the second end of the shaft includes: a loop.

19. A single use ocular surgical tool for the mechanical retraction of an iris comprising in combination:
    a longitudinal shaft having a first end and a second end;
    a hook formed onto the first end of the shaft; and means for stiffening the shaft between the first end and the second end, wherein the shaft is used to mechanically retract an iris without causing anterior vaulting of the iris; and a reusable transparent storage tube open at both ends for holding the longitudinal shaft and viewing the orientation location of the hook.

* * * * *